US00PP26184P3

(12) United States Plant Patent
Scheffers

(10) Patent No.: US PP26,184 P3
(45) Date of Patent: Dec. 1, 2015

(54) ***MEDINILLA* PLANT NAMED 'RS003'**

(50) Latin Name: *Medinilla miniata×magnifica*
Varietal Denomination: RS003

(71) Applicant: Robertus Scheffers, Monster (NL)

(72) Inventor: Robertus Scheffers, Monster (NL)

( * ) Notice: Subject to any disclaimer, the term of this patent is extended or adjusted under 35 U.S.C. 154(b) by 84 days.

(21) Appl. No.: 13/987,198

(22) Filed: Jul. 9, 2013

(65) Prior Publication Data

US 2015/0020257 P1 Jan. 15, 2015

(51) Int. Cl.
*A01H 5/02* (2006.01)

(52) U.S. Cl.
USPC ..... Plt./263.1

(58) Field of Classification Search
USPC ..... Plt./226, 263.1
CPC ..... A01H 5/00
See application file for complete search history.

(56) References Cited

U.S. PATENT DOCUMENTS

| | | | |
|---|---|---|---|
| 3,943,965 | A | 3/1976 | Matalena |
| 4,786,088 | A | 11/1988 | Ziu |
| 5,433,191 | A | 8/1994 | McAtamny |
| 6,032,699 | A | 3/2000 | Cochran et al. |
| 6,123,110 | A | 9/2000 | Smith et al. |
| 6,405,135 | B1 | 6/2002 | Adriany et al. |
| 6,489,894 | B2 | 12/2002 | Berg |
| 6,614,354 | B2 | 9/2003 | Haines et al. |
| 6,970,808 | B2 | 11/2005 | Abhulimen et al. |
| 7,441,441 | B2 | 10/2008 | Omer |
| 7,500,489 | B2 | 3/2009 | Folkers |
| 2005/0212285 | A1 | 9/2005 | Haun |

FOREIGN PATENT DOCUMENTS

| | | | |
|---|---|---|---|
| CA | 2416171 | A1 | 7/2004 |
| CN | 1414283 | A | 4/2003 |
| CN | 101749542 | A | 6/2010 |
| DE | 102005018317 | A1 | 10/2006 |
| WO | WO2007087720 | A1 | 8/2007 |

OTHER PUBLICATIONS

CPVO (Community Plant Variety Office), Feb. 15, 2012.*

* cited by examiner

*Primary Examiner* — Keith O. Robinson
(74) *Attorney, Agent, or Firm* — Cassandra Bright

(57) ABSTRACT

A new and distinct *Medinilla* cultivar named 'RS003' is disclosed, characterized by large dark pink flowers, large green leaves and its suitability for commercial production. The new variety is a *Medinilla*, normally produced as an ornamental plant.

1 Drawing Sheet

Latin name of the genus and species: *Medinilla miniata× magnifica.*

Variety denomination: 'RS003'.

BACKGROUND OF THE INVENTION

The new *Medinilla* cultivar is a product of a planned breeding program conducted by the inventor, Robertus H. M. Scheffers, in Monster, the Netherlands. The objective of the breeding program was to produce new *Medinilla* varieties for ornamental commercial applications. The new variety is a product of crossbreeding that occurred during 2008, at a commercial nursery in Monster, Netherlands.

The seed parent is an unpatented, unnamed variety of *Medinilla miniata*. The pollen parent is an unpatented, unnamed variety of *Medinilla magnifica*. The new variety was discovered in 2010 by the inventor in a group of seedlings resulting from the 2008 crossing, in a commercial nursery in Monster, Netherlands.

Asexual reproduction of the new cultivar has been performed by vegetative cuttings. This was first performed at a commercial nursery in Monster, Netherlands in 2010 and has shown that the unique features of this cultivar are stable and reproduced true to type in successive generations.

SUMMARY OF THE INVENTION

The cultivar 'RS003' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RS003'. These characteristics in combination distinguish 'RS003' as a new and distinct *Medinilla* cultivar:

1. Large flowers.
2. Large green leaves.
3. Suitability for ornamental commercial applications.
4. Dark pink flower color.

PARENT COMPARISON

Plants of the new cultivar 'RS003' are similar to plants of the seed parent, *Medinilla miniata* in most horticultural characteristics, however, plants of the new cultivar 'RS003' produce a much darker flower color than the seed parent.

Plants of the new cultivar 'RS003' are similar to plants of the pollen parent; *Medinilla magnifica* in most horticultural characteristics, however, plants of the new cultivar 'RS003' produce lighter green leaves and darker pink flowers than the pollen parent. 'RS003' also produces longer peduncles than the pollen parent.

COMMERCIAL COMPARISON

Plants of the new cultivar 'RS003' are best compared to *Medinilla* 'RS005', filed concurrently. While the two cultivars are similar in most horticultural characteristics, 'RS003' differs from 'RS005' in the following characteristics;

1. 'RS003' has shorter lateral branches.
2. 'RS003' has larger foliage.
3. 'RS003' has smaller inflorescence with shorter peduncles.
5. Inflorescence of 'RS003' have more individual flowers than inflorescence of 'RS005'.
6. Flower bracts of 'RS003' are larger than bracts of 'RS003'.

BRIEF DESCRIPTION OF THE PHOTOGRAPH

The accompanying photograph in FIG. 1 illustrates in full color a close up of typical flowers and foliage of 'RS003'.

The plant shown is 50 weeks old from a rooted cutting grown in a 2 liter pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RS003' plants grown outdoors in Monster, Netherlands. The growing temperature ranged from 20° C. to 23° C. during the day and from 20° C. to 23° C. during the night. General light conditions are bright, normal sunlight. Measurements and numerical values represent averages of typical plant types.

Botanical classification: *Medinilla miniata×magnifica* 'RS003'.

PROPAGATION

Time to initiate roots: Summer: 21 to 28 days at approximately 20-23° C. Winter: 28 to 35 days at approximately 20-23° C.

Root description: Moderately dense, non-fleshy, non-fibrous, moderately thick, colored Near Greyed-Orange RHS N170A to N170B.

PLANT

Age of plant described: 50 weeks from a rooted cutting.

Growth habit: Upright and spreading, overall plant shape: flattened globular.

Pot size of plant described: 2 liter commercial pot.

Height: 29.0 cm.

Plant spread: At widest: 63.0 cm, at narrowest: 47.0 cm.

Growth rate: Moderate.

Branching characteristics: Not very free branching.

Quantity of primary lateral branches: Average: 3.

Characteristics of primary lateral branches:

*Length*.—Average 13.7 cm.

*Diameter*.—Lateral branches flattened, average diameter at widest: 1.5 cm, average diameter at narrowest: 0.7 cm.

*Color*.—Yellow-green; near RHS 144A, margins (of flattened branches) greyed-yellow; near RHS 161A and 161B.

*Texture*.—Glabrous, moderately glossy, flattened margins.

*Strength*.—Strong.

Internode length: Average: 13.7 cm.

FOLIAGE

Leaf:

*Arrangement*.—Opposite.

*Shape*.—Ovate.

*Quantity*.—Approximately 4 per branch (2 pairs).

*Average overall length*.—Average: 28.5 cm.

*Average overall width*.—Average: 16.7 cm.

*Apex*.—Short apiculate.

*Base*.—Truncate.

*Margin*.—Entire, coarsely undulate.

*Texture of top surface*.—Glabrous, veins furrowed.

*Texture of lower surface*.—Glabrous, ridges due to furrowed venation.

*Appearance*.—Leathery, shiny.

*Aspect*. Very slightly carinate, margins coarsely undulate.

*Color*.—Young foliage upper side: Yellow-green; near RHS 147A. Young foliage under side: Yellow-green; in between near RHS 144B and 147D. Mature foliage upper side: Green to yellow-green; in between near RHS 139A and 147A but slightly. Mature foliage under side: Yellow-green; in between near RHS 147D and 148D.

*Venation*.—Type: Camptodrome. Venation color upper side: Yellow-green; in between near RHS 144B and 145A. Venation color under side: Yellow-green; near RHS 146D.

*Petiole*.—No petioles present, leaves sessile.

*Stipule description*.—No stipules present.

FLOWER

Natural flowering season: April to June in the Philippines.

Typical commercial flowering technique and time: To get the plant into flowering, keep the plant at 18 degrees Celsius for about ten weeks. Year around flowering occurs under the condition that plants receive this cold treatment.

Days to flowering from rooted cutting: 50 weeks.

Inflorescence and flower type and habit: Panicle.

Rate of flower opening: 13 to 16 weeks from bud to fully opened flower.

Inflorescence longevity on plant: Approximately 20 weeks of flowering from first buds to exhausted flowering.

Persistent or self-cleaning: Self-cleaning.

Inflorescence:

*Length*.—Average: 11.8 cm.

*Diameter*.—Average: 11.8 cm.

*Aspect*.—Pendulous.

*Number of flowers*.—Per inflorescence, average: 250.

Bud:

*Shape*.—Obovate.

*Length*.—Average: 1.2 cm.

*Diameter*.—Average: 0.7 cm.

*Color*.—Red-purple; near RHS 58A.
*Texture*.—Glabrous.

Flower size:
*Diameter*.—Average: 2.1 cm.
*Depth*.—Average: 2.3 cm.
*Aspect*.—Outward to pendulous.

Petals:
*Quantity*.—5.
*Arrangement*.—Rotate.
*Shape*.—Near obovate.
*Length*.—Average: 1.0 cm.
*Width*.—Average: 0.9 cm.
*Apex*.—Obtuse.
*Base*.—Cuneate; fused into an urn-shaped hypanthium.
*Margin*.—Entire.
*Texture, upper and lower surfaces*.—Glabrous.
*Appearance*.—Slightly glossy.
*Color*.—When opening, upper surface: Red-purple; near RHS 61D, lighter towards the margins; near RHS 68A and 68B. When opening, lower surface: Red-purple; near RHS 68A to 68B. Fully opened, upper surface: Red-purple; near RHS 68A to 68B. Fully opened, lower surface: Red-purple; near RHS 68B. Aging: Not fading.

Sepals:
*Arrangement*.—Rotate, fused and part of an urn-shaped hypanthium.
*Quantity*.—5.
*Texture*.—Glabrous.
*Length*.—0.8 cm.
*Width*.—Fused into an urn-shaped hypanthium, average width of hypanthium: 0.75 cm.
*Shape*.—Fused into an urn-shaped hypanthium.
*Apex*.—Since sepals cannot be seen as separate sepals the apex cannot be described.
*Base*.—Fused into an urn-shaped hypanthium.
*Margin*.—No margins visible; sepals fused into an urn-shaped hypanthium.
*Color, interior and exterior*.—Red-purple; near RHS 58B, top on exterior tinged white; near RHS 155A.

Bracts:
*Arrangement*.—Opposite.
*Quantity*.—8.
*Texture*.—Glabrous.
*Length*.—Average: 7.4 cm.
*Width*.—Average: 5.3 cm.
*Shape*.—Broad ovate.
*Apex*.—Acute.
*Base*.—Truncate.
*Margin*.—Entire.
*Color, immature, interior*.—Red-purple; near RHS 58D, veins darker; near RHS 58C, top tinged yellow-green, near RHS 146B and 146D.
*Color, immature, exterior*.—Red-purple; near RHS 58D, veins darker; near RHS 59D, top tinged yellow-green, near RHS 144B and 146D.
*Color, mature, interior*.—Red-purple; near RHS 58D, veins slightly darker; near RHS 63C.
*Color, mature, exterior*.—Red-purple; near RHS 58D, veins darker; near RHS 58C.

Peduncles:
*Length*.—Average: 16.7 cm.
*Diameter*.—Peduncles flattened quadrangulate, average diameter at widest: 1.1 cm, average diameter at narrowest: 0.6 cm.
*Angle*.—Peduncle straight on top of lateral branch, but due to the weight of the inflorescence the peduncle is bend to straight vertical (about 90° to soil level/horizontal).
*Strength*.—Very strong.
*Texture*.—Glabrous, matte.
*Color*.—Yellow-green; near RHS 145B and 145C, strongly tinged margined (peduncle quadrangular) greyed-purple; near RHS 184B. Secondary peduncles greyed-purple; near RHS 184C and 184D.

Pedicels:
*Length*.—Average: 0.9 cm.
*Diameter*.—Average: 0.2 cm.
*Angle*.—About 40° to peduncle.
*Strength*.—Moderately strong.
*Texture*.—Glabrous, matte.
*Color*.—Red-purple; near RHS 58C.

Fragrance: No fragrance.

REPRODUCTIVE ORGANS

Stamens:
*Number*.—Average: 10.
*Length*.—Approximately 1.6 cm.
*Diameter*.—Approximately 0.15 cm.
*Color*.—Yellow; near RHS 3C.

Anthers:
*Shape*.—Filaments typically elbow-shaped; basifixed, linear.
*Length*.—Approximately 0.65 cm.
*Diameter*.—Approximately 0.15 cm.
*Color*.—Purple; near RHS 79C, and red-purple; 72C, base yellow; near RHS 7A.
*Pollen*.—No pollen detected.

Pistil:
*Position*.—Growing from the center of each flower, direction downward, but stigma pointed upward due to curvature of style.
*Number*.—Average: 1.
*Length*.—Average: 1.3 cm.
*Style*.—Length: Average: 1.25 cm. Color: Red-purple; near RHS N57B.
*Stigma*.—Shape: Pointed. Color: Red-purple; near RHS N57A. Ovary Color: White; near RHS 155C, outside colored red-purple; near RHS 58B.

OTHER CHARACTERISTICS

Seeds and fruits: No seeds-fruits detected to date.

Disease/pest resistance: Neither Resistance nor susceptibility to normal diseases and pests of the Genus observed.

Temperature tolerance: 10° C. to 30° C. temperature tolerance range.

What is claimed is:

1. A new and distinct cultivar of *Medinilla* plant named 'RS003' as herein illustrated and described.

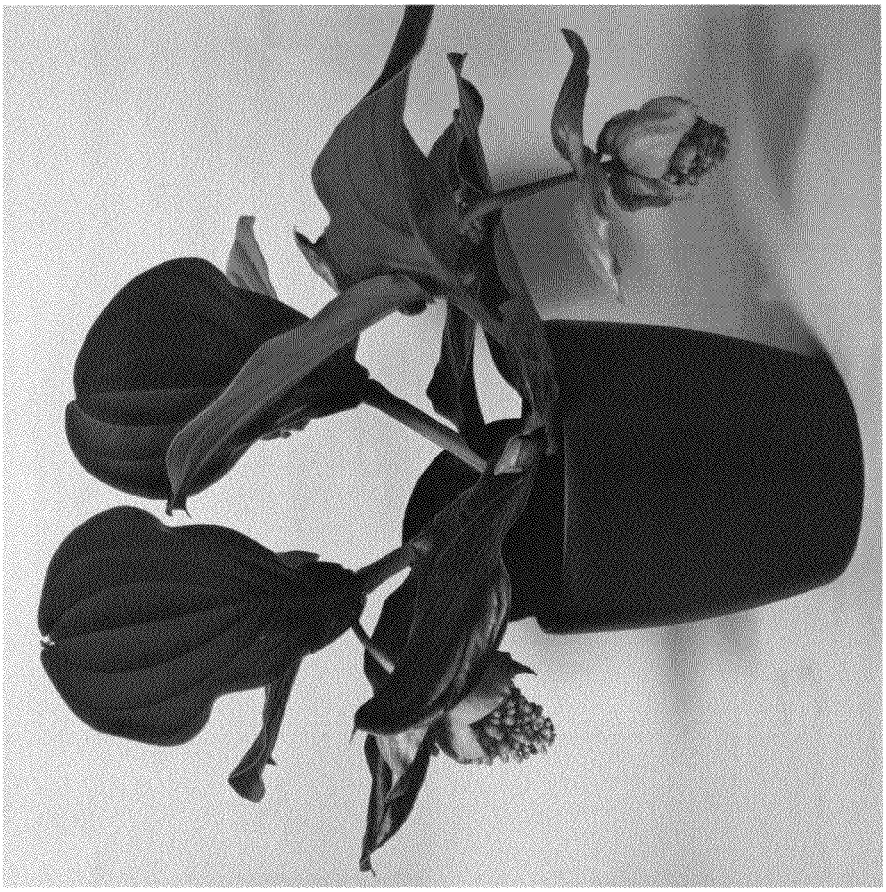

* * * * *